United States Patent
Fan

(10) Patent No.: US 8,961,418 B2
(45) Date of Patent: Feb. 24, 2015

(54) SOLVING FOR SHEAR WAVE INFORMATION IN MEDICAL ULTRASOUND IMAGING

(75) Inventor: Liexiang Fan, Sammamish, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 407 days.

(21) Appl. No.: 12/898,957

(22) Filed: Oct. 6, 2010

(65) Prior Publication Data

US 2012/0089019 A1    Apr. 12, 2012

(51) Int. Cl.
| | | |
|---|---|---|
| A61B 8/00 | (2006.01) | |
| A61B 8/08 | (2006.01) | |
| G01S 7/52 | (2006.01) | |
| G01S 15/89 | (2006.01) | |
| A61B 8/14 | (2006.01) | |

(52) U.S. Cl.
CPC ............ *A61B 8/485* (2013.01); *G01S 7/52042* (2013.01); *G01S 15/8906* (2013.01); *A61B 8/14* (2013.01); *A61B 8/488* (2013.01)
USPC ........................................................ 600/438

(58) Field of Classification Search
USPC ........................................................ 600/438
See application file for complete search history.

(56) References Cited

U.S. PATENT DOCUMENTS

| | | | |
|---|---|---|---|
| 5,810,731 A | | 9/1998 | Sarvazyan et al. |
| 6,561,981 B2 * | | 5/2003 | Bonnefous .................... 600/443 |
| 6,770,033 B1 | | 8/2004 | Fink et al. |
| 6,770,034 B2 * | | 8/2004 | Sunagawa et al. ............ 600/443 |
| 7,252,004 B2 | | 8/2007 | Fink et al. |
| 2007/0106157 A1 * | | 5/2007 | Kaczkowski et al. ......... 600/438 |
| 2010/0016718 A1 * | | 1/2010 | Fan et al. ...................... 600/438 |
| 2010/0138163 A1 | | 6/2010 | Gallippi et al. |

OTHER PUBLICATIONS

Search Report and Written Opinion in counterpart French application No. 11 03043, filed Oct. 6, 2011, dated Feb. 24, 2014, 11 pages total (including English translation).
Bouchard, et al., *Image quality, tissue heating, and frame rate trade-offs in acoustic radiation force impulse imaging*, IEEE Transactions on Ultrasonics, Ferroelectrics and Frequency Control, IEEE, US, vol. 56, No. 1, Jan. 1, 2009, pp. 63-76, XP011267404.
Dahl, et al., *A parallel tracking method for acoustic radiation force impulse imaging*, IEEE Transactions on Ultrasonics, Ferroelectrics and Frequency Control, IEEE, US, vol. 54, No. 2, Feb. 1, 2007, pp. 301-302, XP011168520.

* cited by examiner

*Primary Examiner* — Jonathan Cwern

(57) ABSTRACT

A shear wave velocity solution is provided for medical ultrasound imaging. Rather than determining shear wave information for each location based on distance from the origin of the shear wave and time to peak displacement for the location, displacement profiles resulting from different combinations of origin and detection locations are correlated. Shear information is detected using displacements from a diverse spatial combination of transmission locations and detection locations. The correlation combination is used in a same function for simultaneously solving for the delays for multiple lateral locations. Spatial diversity and layered correlation may provide for more accurate shear wave estimation.

8 Claims, 3 Drawing Sheets

SOLVING FOR SHEAR WAVE INFORMATION IN MEDICAL ULTRASOUND IMAGING

BACKGROUND

The present embodiments relate to ultrasound imaging. In particular, shear wave information is determined for ultrasound imaging.

Shear velocity detection is used in various diagnostic applications, such as assessing liver disease. The shear velocity may indicate tissue properties, allowing detection of tumors or other regions. However, the detection accuracy may be insufficient for comfort in other applications.

For shear wave detection, an ultrasound pushing pulse is fired along a scan line. The pushing pulse generates a shear wave, causing displacement of tissue. The displacement is detected. To detect the shear wave velocity, multiple pushing pulses along a same scan line may be used. Even where multiple pushing pulses are not fired along a same scan line, the pushing pulses are sequentially fired along adjacent scan lines. Additions of shear waves and tissue resonance caused by multiple pushes at the same or adjacent locations may result in artifacts or a lack of sufficient accuracy for some applications.

BRIEF SUMMARY

By way of introduction, the preferred embodiments described below include methods, instructions, and systems for solving for shear wave information in medical ultrasound imaging. Rather than determining shear wave information for each location based on distance from the origin of the shear wave and time to peak displacement for the location, displacement profiles resulting from different combinations of origin and detection locations are correlated. Shear information is detected using displacements from a diverse spatial combination of transmission locations and detection locations. The correlation combination is used in a same function for simultaneously solving for the delays for multiple lateral locations. Spatial diversity and layered correlation may provide for more accurate shear wave estimation.

In a first aspect, a non-transitory computer readable storage medium has stored therein data representing instructions executable by a programmed processor for solving for shear wave information in medical ultrasound imaging. The storage medium includes instructions for determining first displacement of tissue as a function of time caused by a first shear wave in response to a first acoustic transmission along a first scan line, the first displacement being on a fourth scan line spaced from the first scan line by at least second and third scan lines; determining second displacement of tissue as a function of time caused by a second shear wave in response to a second acoustic transmission along the third scan line, the second displacement being on the fourth scan line; determining third displacement of tissue as a function of time caused by a third shear wave in response to a third acoustic transmission along the first scan line, the third displacement being on the second scan line; calculating, for each of a plurality of lateral locations, a delay corresponding to a maximum of correlations of the first and second displacements, of the first and third displacements, and of the second and third displacements; and calculating shear velocity in tissue for each of the plurality of lateral locations as a function of the respective delay.

In a second aspect, a method is provided for solving for shear wave information in medical ultrasound imaging. First shear waves in tissue are detected at a same location caused by transmissions at different locations. Second shear waves in tissue are detected at different locations caused by transmissions at a same location. A shear velocity is calculated as a function of both the first and second detected shear waves. An image represents the tissue as a function of the shear velocity.

In a third aspect, a system is provided for solving for shear wave information in medical ultrasound imaging. A receive beamformer is operable to output data representing spatial locations as a function of received acoustic signals. A processor is configured to estimate tissue displacements as a function of the output data, compute correlation coefficients for at least one pair of the tissue displacements from different ones of the spatial locations, solve for a traveling time based on the correlation coefficients, and generate an image as a function of the traveling time. A display is operable to display the image.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Shear information is detected using displacements from a diverse spatial combination of transmission locations and detection locations. To avoid shear waveform ambiguity introduced by repeating excitation (pushing pulse) on the same spatial location, an interleaving sequence is used. Due to the interleaving, the sequence may also reduce beam overlap, reducing an amount of temperature rise. The sequence may have superior shear wave signal strength as compared to multiple transmissions along the same scan line. The strength may allow detection that is more reliable and robust.

Instead of detecting the time-to-peak of the shear wave, the travel time is determined by using correlation of the shear wave response from locations which are associated with the sequencing strategy. The travel time estimation problem is treated as an optimization problem in the correlation coefficient space, resulting in an optimal solution compared with searching time-to-peak or solving the Helmholtz equation.

In one embodiment, at least one distance value for a given tissue type and imaging system device is determined. Spatial interleaving of the excitation pulses is used to minimize tissue thermal effect. The locations of spatial distribution of shear wave detection pulses are diversified. Data is acquired using the diverse locations with interleaved transmissions, allowing for correlation determination of the delay or travel time for the shear wave.

In another embodiment, correlation coefficients are computed for at least one pair of shear wave displacement temporal profiles. The traveling time of the shear wave between each given distance is estimated from the correlation coefficients. The traveling time is inverted, and the result is multiplied by the distance to obtain shear velocity. Other embodiments are possible.

Figure 1:
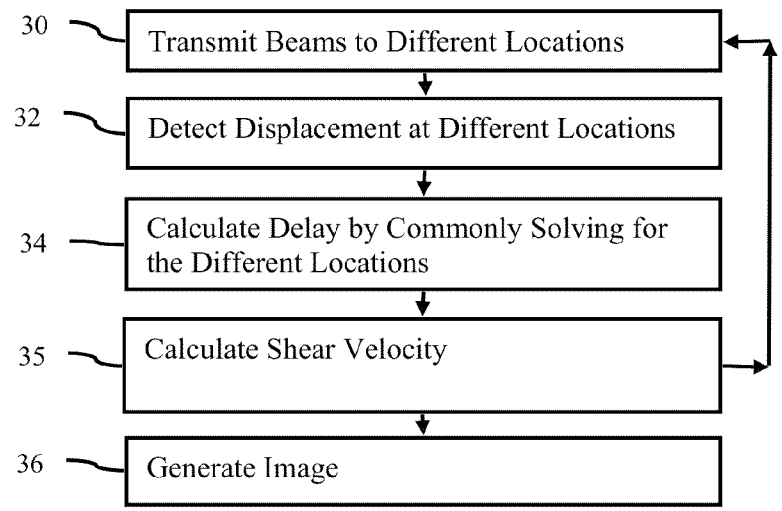
FIG. 1 is a flow chart diagram of one embodiment of a method for solving for shear wave information in medical ultrasound imaging.

FIG. 1 shows a method for solving for shear wave in medical ultrasound imaging. The method is implemented by the system of FIG. 6 or a different system. Additional, different, or fewer acts may be provided. For example, act 35 is not performed. Instead, another shear wave characteristic is determined. As another example, act 36 is not performed. The iteration or repetition represented by the arrows from act 35 to act 30 may not be provided in other embodiments. The acts are performed in the order described or shown, but may be performed in other orders.

In act 30, acoustic pulses are transmitted for generating a shear wave. Excitations are transmitted from an ultrasound transducer. The excitations are acoustic energy. The acoustic energy is focused, resulting in one or more beams for each transmission. The excitations are focused using a phased array and/or mechanical focus. The excitations may be unfocused in one dimension, such as the elevation dimension. The excitations are transmitted into tissue of a patient. The excitations are focused at a location to allow detecting of the resulting shear wave, such as a tissue location surrounding and including a possible tumor.

Figure 2:
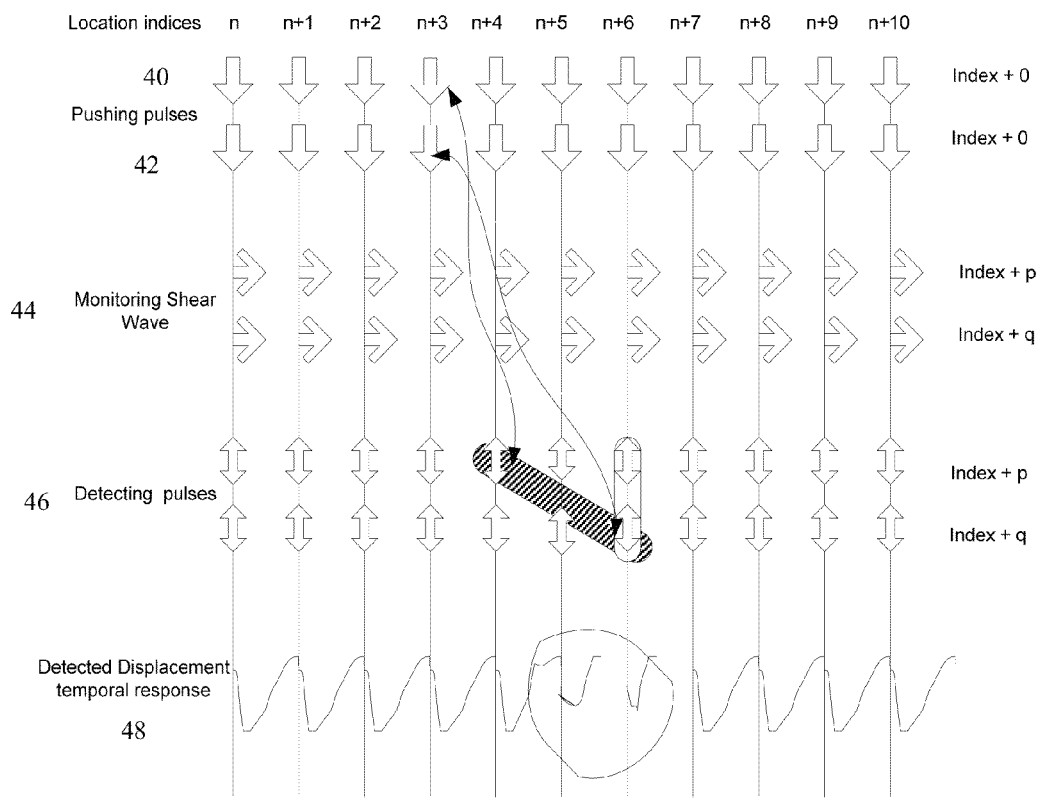
FIG. 2 is a graphic illustration of an example transmit and displacement detection sequence.

The transmissions are focused at different locations. To scan a region of a patient for generating shear waves, one or more transmissions are focused at a same location. Other transmissions are focused at other locations. The shear wave is generated at the focal region and propagates laterally from the focal region. The shear wave is detected at locations adjacent to and/or spaced from the focal region for any given transmission. The shear wave reduces in amplitude as the wave travels through the tissue. To detect tissue response to shear waves in a region of interest, transmissions are made to other focal regions and detection is performed around the other focal regions. The detection regions from different transmission focal regions overlap. For example, FIG. 2 shows ten scan lines, n through n+10. More or fewer scan lines may be provided. Two or more transmissions for generating shear waves are performed along each scan line, as represented by the arrows for the pushing pulses at 40 and 42. The scan lines for pushing pulses are the same as the scan lines for detection. In alternative embodiments, one or more pushing pulse scan lines are different from receive or detection scan lines.

To generate a shear wave, high amplitude or power excitations are desired. For example, each excitation has a mechanical index of close to but not exceeding 1.9. To be conservative and take into account of probe variation, mechanical index of 1.7 may be used as the upper limit. Greater (e.g., MI exceeding 1.9) or less powers may be used. Transmitting sequentially along the same or adjacent scan lines may cause the tissue to increase in temperature over time. Biological effects may include hyperthermia at tissue temperature of about 41-45° C., protein denaturation at temperatures above 45° C., and tissue necrosis at temperatures above 50° C. Tissue stiffness may be affected even at temperatures below 45° C. At temperatures above 45° C., increases in viscosity and/or stiffness may occur. At temperatures above 50° C., the tissue may have a high stiffness and/or high attenuation. The transmissions may cause biological effects. Alternatively, biological effects are limited by preventing a temperature increase of over 2 degrees Celsius.

Figure 3A:
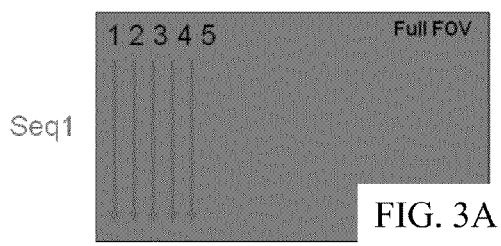
FIGS. 3A-C illustrate different transmit sequences.
Figure 3B:
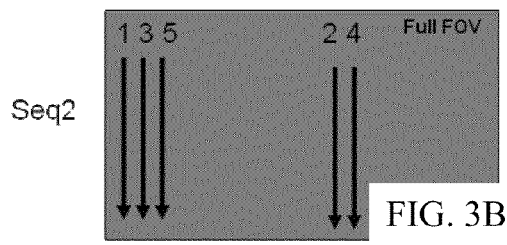
Figure 3C:
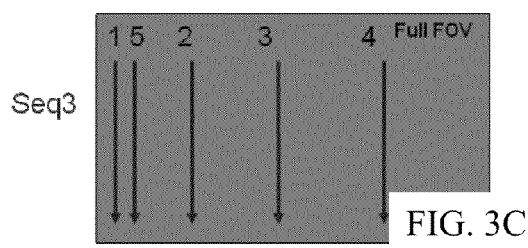

FIGS. 3A-C show three different transmission sequences for generating shear waves at different locations. FIG. 3A shows sequentially transmitting along adjacent scan lines. The scan lines are shown as downward pointing arrows. The transmission order is numbered 1-5. Fewer or additional scan lines may be used.

FIGS. 3B and C show sequences of transmissions to cause less temperature rise over time. The sequential transmissions are performed in an order avoiding immediately sequential transmissions along adjacent scan lines by spatially interleaving the transmissions across scan lines. FIG. 3B shows firing excitations along five scan lines, but doing so in a left/right sequence. The field of view is divided in half—the right and left halves. The first transmission is along a scan line on left side of the left half. The second transmission is along a scan line on the left side of the right half. This pattern continues, ending with a next to last transmission on the right side of the left half and a last transmission on the right side of the right half. Throughout the sequence, the temporally adjacent transmissions in the sequence are spaced by half of the field of view for shear detection (e.g., region of interest).

FIG. 3C shows another possible sequence. In this example, the field of view is separated into quarters. Each quarter is sequentially scanned in an interleaved cycle. Other scan sequences with other divisions, randomization, or temporal/spatial patterns may be used.

Figure 3D:
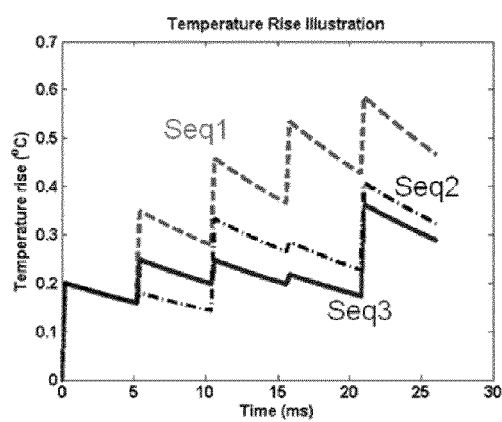
FIG. 3D is an example graph showing temperature effects of the different transmit sequences of FIGS. 3A-C.

FIG. 3D shows a temperature rise associated with the three different sequences of FIGS. 3A-C. The tissue temperature rise is shown in the near field where the acoustic fields of beams heavily overlap. Sequence 1 (dashed line) of FIG. 3A has a greater temperature rise over time. Sequences 2 and 3 (dash-dot line and solid line, respectively) of FIGS. 3B and C have reduced temperature rise.

The temperature may alternatively or additionally be controlled in shear wave estimation by solving for shear wave velocity using additional correlation. To provide this additional correlation, allowing simultaneous solving for delay at multiple lateral locations, phased acquisition sequence with a limited number, such as two, three or four, pushing pulses to the same location is used. At 40 and 42, FIG. 2 represents two phases of pushing pulses or transmissions to generate shear waves. Instead of pushing multiple times (e.g., five, ten, or more) on the same location with short pulse repetition interval (PRI), two or more phases of acquisition are used. Each phase 40, 42 scans across the scan lines in any pattern, such as shown for FIGS. 3A-C. Using just two phases, the excitation PRI for the same spatial location may be very low (on the order 100 ms).

Other transmissions occur. These other transmissions are for detecting the shear waves rather than causing the shear wave. The transmissions for detection may have lower power and/or short pulses and use the same or different scan lines as the pushing pulses to generate the shear waves. The transmissions for detection may have a wider beam profile along at least one dimension, such as laterally, for forming receive samples along a plurality of scan lines.

In act 32, displacement of tissue is determined. The shear wave causes the tissue to move. FIG. 2 shows the displacement for monitoring the shear wave as an arrow at 44. The arrows are shown in one direction, but the shear wave travels in multiple directions. The shear wave may be monitored in one, two, or more directions.

The displacement of the tissue caused by the shear wave is determined over time. When the shear wave is generated, adjacent tissue is not moving until the shear stress propagates. As the shear wave passes a given location, the tissue displaces by an amount or distance that increases to a peak amount and then decreases as the tissue returns to rest. The peak amount is associated with a delay or travel time from the generation of the shear wave at the focal point to when the peak of the shear wave passes another location. This displacement profile over time is determined by tracking the magnitude of the tissue movement over time.

The displacement is detected with ultrasound scanning. To detect the displacement, ultrasound energy is transmitted to the tissue undergoing displacement and reflections of the energy are received. FIG. 2 shows this detection at 46. The transmission and reception for detection are performed multiple times to determine change due to displacement. Any transmission and reception sequence may be used. The detection of displacement may be interleaved with other scanning, such as scanning different regions for displacement separately.

A region of interest is monitored to detect the shear wave. The region of interest is any size, such as 6 mm in lateral and 10 mm in axial. This detection region is monitored by ultrasound. For example, B-mode scans are performed to detect tissue displacement caused by the shear wave. Doppler, color flow, or other ultrasound mode may be used to monitor for the shear wave.

The monitoring is performed for any number of scan lines. For example, four receive beams are formed in response to each transmission. After transmitting the excitation to generate the shear wave, B-mode transmissions are performed repetitively along a single scan line and receptions along four adjacent scan lines. In other embodiments, only a single receive beam or other numbers of receive beams are formed in response to each transmission. Any number of repetitions may be used, such as about 10-120 times. Some of the ultrasound data, such as at the beginning or end of the repetitions, may not be responsive to the shear wave.

As the shear wave propagates through the scan lines, the B-mode intensity may vary. For the monitored scan lines, a sequence of data is provided representing a time profile of tissue motion resulting from the shear wave. For example, data from a plurality of spatial locations (e.g., along the scan lines) is correlated with a reference frame of data or image as a function of time. Any elasticity detection may be used. For each depth or spatial location, a correlation over a plurality of depths or spatial locations (e.g., kernel of 64 depths with the center depth being the point for which the profile is calculated) is performed. Two or three-dimensional displacement in space may be used. One-dimensional displacement along a direction different from the scan lines or beams may be used.

The spatial offset with the highest or sufficient correlation at a given time indicates the amount of displacement. Displacements are determined for a given location at different times. The temporal profile for a given location indicates detection of the shear wave. The profile is examined for a non-noise or single instance of variation. A peak in the profile, with or without temporal low pass filtering, indicates the passing of the shear wave front. The greatest displacement is selected, but the average or other displacement statistic may be used. FIG. 2 shows the detected displacement temporal response at 48.

To monitor a larger region, additional receive beams are formed in response to the same pushing pulse. Alternatively, another shear wave is generated and the transmit beams and receive beams are provided at a different distance from the shear wave generation point. Using the solution described herein, the displacements associated with multiple lateral locations are obtained using only two or more pushing pulses per scan line. For each receive beam location, a time profile of motion information is provided, represented by the ultrasound data. Transmissions along different scan lines to monitor a same shear wave are avoided during formation of the temporal profile to provide higher temporal resolution, but interleaved or shifting scanning positions may be provided.

The discussion above is for one depth. The sampling may be arranged to provide one gate covering the entire axial extent of the region of interest. In another embodiment, samples are obtained at multiple depths for each receive beam. A separate time profile is provided for each axial depth as well as lateral location. Any number of depths may be used, such as about 200 for 5 mm or 400 for 10 mm.

Ultrasound data representing different locations in the region of interest is obtained. The ultrasound data is obtained in real-time with the scanning or obtained from a memory. For each location, the motion information represents the response at different times. Other scanning, monitoring, or techniques may be used to obtain ultrasound data to estimate shear magnitude.

Using displacements arranged in time and lateral location allows estimation of shear velocity with as few as two pushing pulses being fired per scan line. For example, shear waves in tissue are detected at a same location caused by transmissions from different locations; shear waves in tissue are detected at different locations caused by transmissions at a same location; and shear waves in tissue are detected at different locations caused by transmissions at other different locations. This spatial and temporal diversity allows for solving for shear wave with less ambiguity.

FIG. 2 shows using this location diversity. In this pulsing strategy, excitation force is applied twice at each index location (e.g., scan line) to generate shear waves, and the detection pulse sequence is also applied twice to detect the shear wave at other locations. However, each detection pulse sequence corresponds to different locations, resulting in a system with three possible sets of shear wave detecting solutions. One set corresponds to the sequencing detected at the same location but excited at two different locations, the second set corresponds to the sequencing detected a different locations but excited from the same location, and the third set corresponds to the detection and excitation all at different locations. This idea is shown in FIG. 2 as the index offset parameter p and q, and the link between two tube shapes at 46. More or less temporal and spatial diversity may be used, such as providing for additional locations and/or times and associated combinations.

A heterogeneous area is illustrated in FIG. 2 as the oval in the detected displacement responses at 48. The displacement temporal responses are different at locations inside and outside of the heterogeneous area. The heterogeneity of medium makes none of each single set of the above solution perfect.

Figure 4:
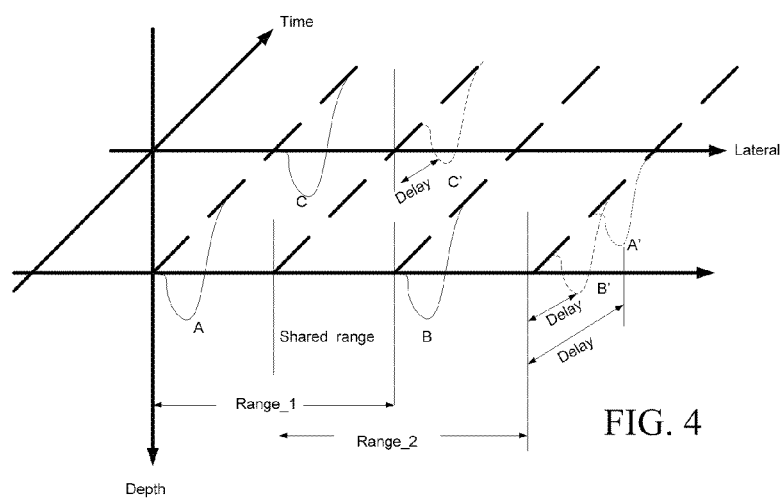
FIG. 4 is a graph showing one example of axial, lateral, and temporal displacement sampling.

FIG. 4 shows one example of spatial and temporal locations of displacement temporal responses and their corresponding excitations. A, B, and C are shear waves generated at corresponding excitation locations (dashed lines). A', B', and C' are shear waves as detected at detection locations. The detection locations are on equally spaced scan lines, but may have other distributions. This example is of three pushing pulses for shear waves A, B, and C and associated detected displacements (A', B', and C') of tissue as a function of time. FIG. 4 represents the process at one depth. The horizontal axis shows lateral spacing where pushing pulses for shear waves A and C are transmitted along a first scan line and the pushing pulse for shear wave B is transmitted along a third scan line. Another horizontal axis represents time, showing pushing pulses for shear waves A and C transmitted along the first scan line occurring at different times. For example, pushing pulses for shear waves A and C correspond to pushing pulses 40, 42 along a same scan line n+3 in FIG. 2. Pushing pulse for the shear wave B is shown transmitted at a same time, but this is relative. The actual transmission occurs in sequence along the third scan line (e.g., scan line n+6 in FIG. 2). The timing of the displacement detection in response to pushing pulses A and B are shown as occurring at the same time to better indicate the relationship of the detected displacements A' and B' on the same, fourth scan line.

In the example of FIGS. 2 and 4, the displacement A' caused by the shear wave A in response to the acoustic transmission along scan line n+3 is detected. This displacement A' is on scan line n+6, shown by the arrow from the second pushing pulse in FIG. 2. The detection is performed with two intervening scan lines. No other intervening scan lines are provided. In alternative embodiments, only one or more than two intervening scan lines are used. The displacement B' caused by the shear wave B in response to the acoustic transmission along the scan line n+5 is detected. This displacement B' is on the scan line n+6, immediately adjacent to the scan line n+5 used for the pushing pulse to generate shear wave B. Additional intervening scan lines may be provided. The displacement C' caused by the shear wave C in response to the acoustic transmission along the same scan line n+3 as pushing pulse for shear wave A is detected. This displacement C' is detected along the immediately adjacent scan line n+4, but one or more intervening scan lines may be provided. FIG. 2 shows an arrow from the pushing pulse 40 on scan line n+3 to the detecting pulse 46 on scan line n+4 to represent C and C'.

Other spatial and temporal relationships may be provided. FIGS. 2 and 4 are examples. Another pushing pulse along scan line n+3 and/or n+5 may be used. Detection of additional displacements along the same or different scan lines with or without additional pushing pulse transmissions may be used (e.g., detecting C" on n+5 in addition to C' on n+4 in response to the same pushing pulse C). FIGS. 2 and 4 show detection occurring on scan lines spaced to the right of the transmissions, but any spacing (e.g., to the left in two-dimensions or front/back in three-dimensions) may be used.

In FIG. 4, AA' and BB' form one pair for detecting the traveling time parameter in range__1. AA' and CC' forms another pair for detecting the traveling time parameter in range__2, respectively. BB' and CC' form another pair for limiting the solution. The range parameters represent a known distance between scan lines. The travel time over range__1 and range__2 may be determined as the delays 1 and 2 from the spatial/temporal pairs. The delay information may be used to determine the velocity or travel time of the shear wave.

In act 34, the spatial diversity is used to calculate the delays. The displacements are correlated to calculate the delay. By considering a range of different possible delays, the displacement profiles are used to solve for the delays associated with different locations in a same calculation. For a given location, the delay corresponding to a maximum correlation of spatially diverse displacements is calculated. Rather than performing one correlation, the maximum is a function of multiple correlations, such as associated with different pairs of displacements. The shear velocity or other shear information is calculated as a function of the detected shear waves using correlation. Where the displacements are determined using correlation, such as for speckle tracking, an additional or layered correlation is used to determine shear information from the displacements.

Conventional wave propagation time is determined according to the following function:

$$\tau_s = \max_{arg(\tau)} c(\tau) = \sum_{t=0}^{T} d(m, n, t) d(u, v, t+\tau) \quad (1)$$

where $\tau$ is the delay, c is a correlation, t is time, d is the displacement, and m, n, u, and v are spatial coordinates in two-dimensions. For example, the two displacement functions are the displacement curves or profiles A' and B'. This maximum correlation may perform adequately in reasonably high signal-to-noise ratio and for less deformed signal waveforms, but may not be adequate in other situations.

To compensate for the issues caused in the transited zone, such as shown in FIG. 2 as the heterogeneous tissue region, spatial diversity is used. Multiple pairs of correlations are used to determine the delay. The spatial and temporal diversity may be used to determine spatial distribution of the shear waves and time duration of the shear waves for each of a plurality of lateral locations. Group behavior of cross correlation is used in searching for the maximum correlation. For each lateral location, y, a range of possible delays is used to determine the delay associated with the maximum correlation. The correlation function of the full lateral span at the same depth may be obtained as a two-dimensional matrix c (y, $\tau$). The delay for each of a plurality of lateral locations is solved simultaneously. The delay for shear velocity may be solved for a plurality of the scan lines at a same time as part of a same function. Correlation of the displacements from the different locations is computed for at least one pair of shear wave displacement temporal profiles. One function is used to output a matrix of delays for corresponding locations.

The displacement temporal response is denoted as d(i, j, t) where indices i and j represent the excitation location index (e.g., scan line) and the tracking location index (e.g., scan line), respectively. Correlation is used to detect the pulse delay between two pairs of the displacement curvers, d (i, j, t). That is {d(i,i+p,t), d(i,i+q), t)}, {d(i,i+p, t), d(i+p−q,i+p, t)}. Another pair {d(i,i+q), t), d(i+p−q,i+p, t)} contributes to the determination of heterogeneous zone. In the example of FIG. 4, one pair is A'B', another pair is A'C', and the pair contributing to the determination of the heterogeneous zone is B'C'.

Other pairs may be used, such as where additional pushing pulse transmissions and/or detections are performed. Any spatially, temporally, or spatially and temporally diverse pairs of displacements may be used. The computing is a function of a distance between scan lines, such as provided by detecting displacement for pushing pulses along a same scan line at different scan lines. The range between scan lines is used to determine the range. The range is used with the delay to determine the velocity of the shear wave.

One example function calculates a sum of the correlations of three different pairs of displacements. Detected shear waves from different transmissions along a same scan line and/or different detection scan lines are correlated with each other. By assuming $\tau$ maintains a continuous change in the same depth, then the $\tau$ value for the same depth and along full lateral span, denoted as a boundary line or curve $\Gamma_\tau$, is obtained by solving the cost function defined as:

$$\Gamma_\tau = \max \sum_{y=0}^{Y_{max}} \{\alpha c_1(y, \tau) + \beta c_2(y, \tau)\} - \gamma c_3(y, \tau) \|\dot{t}(y)\| \quad (2)$$

where:

$$c_1(y, \tau) = \sum_{t=0}^{T} d(i, i+p, t) d(i+p-q, i+p, t+\tau) \quad (3)$$

$$c_2(y, \tau) = \sum_{t=0}^{T} d(i, i+p, t) d(i, i+q, t+\tau)$$

$$c_3(y, \tau) = \sum_{t=0}^{T} d(i, i+p, t) d(i+p-q, i+q, t+\tau)$$

The curve is represented as a matrix of delays $\tau$ and lateral location y, where $\tau'(y)$ is a first, second, third or other derivative of $\tau$ over y. $\alpha,\beta,\gamma$ are weighting parameters. These weighting parameters can be set to real number 1.0, set to other numbers, or may be a function of the $\tau$. Any range and number of values for the delay may be used, such as 32 possible values of $\tau$ over a unity range of 0 to 100 being considered. The curve of the maximum correlation coefficient is solved for each depth by combining all the information from the available shear wave propagation. In alternative embodiments, additional pair terms or correlations may be used. Different diversity combinations may be used.

Using equation (2) or other correlation function with multiple diverse pair terms may reduce the variance due to the excitation at two locations with different modulus; may adaptively handle medium heterogeneity by introducing the correlation term $c_3$ (e.g., correlation of B'C'); and may reduce the error by applying the neighboring constraints.

As shown in FIG. 4, the estimation of the delay, $\tau$, is different for the pair of data used in computing the correlation function. Pair data $\{d(i,i+p,t), d(i,i+q), t)\}$ (A'B' correlation) estimates the mean time delay in range_1, and pair $\{d(i,i+p, t), d(i+p-q,i+p, t)\}$ (A'C' correlation) estimates the mean time delay in range_2. There is a shared range in these two estimations. The fine estimate ($\tau$) between each group of adjacent lines is obtained by unwrapping $\Gamma_\tau$ in the full lateral span given the known values at both ends. The full lateral span may be across the entire region of interest (e.g., tens of scan lines), but may be across a sub-set of the region. The known values are obtained by the slightly different sequencing of the excitation and detection pulses that is specific to the ends. At both ends of the imaging field of view, the detection C' is at the same location of C, and excitation B is at the same location of the tracking pulse B', therefore the estimated traveling time is the average value from A to A'. The following equations are used to solve the $\tau$ value of the interval between each group of beams:

$$\tau = \begin{cases} \tau_0, & \text{end} \\ \frac{1}{2}\tau_{i-1} + \tau_i + \frac{1}{2}\tau_{i+1}, & \text{middle} \\ \tau_{N-1}, & \text{end} \end{cases} \quad (4)$$

The sequencing at both ends provides the estimation of $\tau_0$ and $\tau_{N-1}$.

Figure 5:
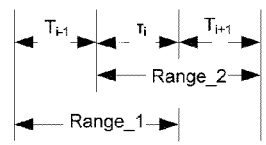
FIG. 5 is an example chart showing range and delay relationships.

FIG. 5 represents the middle of equation (4). The method to unwrap the delay $\tau$ values given the known values at the end points $\tau_0$ and $\tau_{N-1}$ may be described as recursive solution equations. From the order low to high given $\tau_0$, the following equations hold:

$$a(n)\tau_i + \frac{1}{2}\tau_{i+1} = b(n) \quad (5)$$

$$\begin{cases} a(0) = 1, a(1) = 1, a(2) = 1 - \frac{1}{4}, a(n) = 1 - \frac{1}{4a(n-1)} \\ b(n) = \hat{\tau}_n - \frac{b(n-1)}{2a(n-1)}, b(0) = \tau_0 \end{cases} \quad (6)$$

All the a(n) and b(n) may be calculated so that the equation (4) reduces to two unknown variables. Given this equations system and the fact that $\tau_{N-1}$ is known, equations (5) can be solved from the high to low order of the index, providing $\tau$ for each group of adjacent beams. The same method is used resolve the individual $\tau$ for parallel beam acquisition. For instance, when four parallel beams indexed from 0 to 4 are used in tracking pulses, each of the indexed beams can be solved through equations (4) to (6). The weighted coefficient ½ in equation (4) is changed by taking into account of the different distance between each indexed beam.

In act 34, the shear velocity is calculated as a function of the delay and lateral location. Shear velocity is detected for the different spatial locations of the tissue. The shear velocity in tissue for each of the plurality of lateral locations is calculated as a function of the respective delay.

The shear velocity is obtained from the traveling time or delay ($\tau$) and the known distance (e.g., range) between scan lines. The time and distance to the location determine the velocity. The distance is known from the scan line spacing (i.e., the transmit beam position for generating the shear wave and the receive beam position for detecting the shear wave).

Any modulus or shear value may be estimated as an alternative or in addition to shear velocity. Tissue modulus values represent the hardness or stiffness at the locations. For example, the shear modulus of tissue is estimated. In alternative embodiments, Young's modulus is estimated. In other embodiments, other shear values are estimated, whether quantitative or qualitative.

The shear modulus is given by $g=\rho v_s^2$, where $\rho$ is density, and $v_s$ is estimated shear velocity. In one embodiment, the tissue moduli or shear information, such as the shear modulus, is determined as a function of the strain or displacement and the moduli or shear information. For example, the shear modulus for each sample location is determined by iteratively solving a diffusion equation. Assuming a Poisson's ratio of 0.5 or using a known Poisson's ratio, the shear modulus at different locations is calculated iteratively as a function of the strain field at different times or under different stress for the different locations and the shear modulus.

The acts are repeated for other scan lines and/or other depths. For example, acts 30, 32, 34, and 35 are performed again for each of one or more depths. The acts may be performed again for other laterally spaced locations. For example, FIG. 4 shows one part of the overall sequence. The various correlations for different lateral locations y are provided in solving equation (3). Alternatively, other lateral portions are handled separately, such as in unique groups of four scan lines. Alternatively, the pushing pulse and detected displacement pairs or information may be used for other solutions or parts of the region of interest. For example, B and B' may be used as the C and C' pair for a solution.

In act 36, an image is generated. The image represents the tissue as a function of the shear velocity or other shear information. The region for shear information may be a sub-set or region of interest in an image representing a larger area or volume of the patient. For example, the shear velocity modulates color for pixels in a region in a gray-scale modulated B-mode image. The image may represent displacement information, such as shear or moduli (e.g., the shear moduli) for the different locations. The display grid may be different from the scan grid and/or grid for which displacements are calculated. Color, brightness, luminance, hue, or other characteristic is modulated as a function of the shear information.

Figure 6:
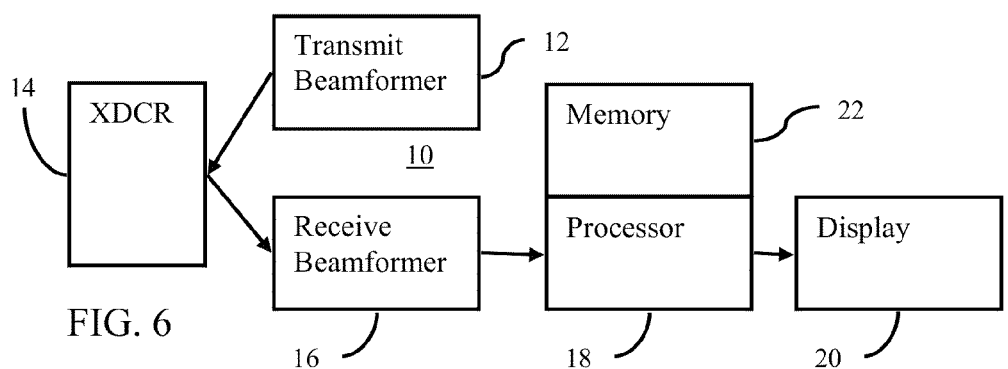
FIG. 6 is one embodiment of a system for solving for shear wave information in medical ultrasound imaging.

FIG. 6 shows one embodiment of a system 10 for solving for shear wave information in medical ultrasound imaging. The system 10 implements the method of FIG. 1, FIG. 2, FIG. 4 or other methods. The system 10 includes a transmit beamformer 12, a transducer 14, a receive beamformer 16, an image processor 18, a display 20, and a memory 22. Additional, different or fewer components may be provided. For example, a user input is provided for manual or assisted designation of a region of interest for which shear information is to be obtained. As another example, an additional HIFU transducer 24 is provided for treating the tissue. The system 10 is a medical diagnostic ultrasound imaging system. In alternative embodiments, the system 10 is a personal computer, workstation, PACS station, or other arrangement at a same location or distributed over a network for real-time or post acquisition imaging.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. Upon transmission of acoustic waves from the transducer 14 in response to the generated waves, one or more beams are formed. A sequence of transmit beams are generated to scan a two or three-dimensional region. Sector, Vector®, linear, or other scan formats may be used. The same region is scanned multiple times. For flow or Doppler imaging and for strain imaging, a sequence of scans is used. In Doppler imaging, the sequence may include multiple beams along a same scan line before scanning an adjacent scan line. For shear wave imaging, any sequence may be used, such as shown in FIGS. 3A-C. One, two, or more transmit beams for generating shear waves may be formed along each scan line prior to scanning another scan line or may be interleaved. For example, the acquisition sequence is separate from the correlation calculation. A memory stores data to provide the displacement information for the correlation. In alternative embodiments, the transmit beamformer 12 generates a plane wave or diverging wave for more rapid scanning.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. For example, the transducer 14 is a two-dimensional PZT array (e.g., about 3,000 elements). Receive signals are generated in response to ultrasound energy (echoes) impinging on the elements of the transducer 14. The elements connect with channels of the transmit and receive beamformers 12, 16.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to each transmission for detection. The receive beamformer 16 outputs data representing spatial locations using the receive acoustic signals. Relative delays and/or phasing and summation of signals from different elements provide beamformation. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental or other band.

The receive beamformer 16 outputs beam summed data representing spatial locations. Data for a single location, locations along a line, locations for an area, or locations for a volume are output. Dynamic focusing may be provided. The data may be for different purposes. For example, different scans are performed for B-mode or tissue data than for shear wave detection. Alternatively, the B-mode data is also used to determine displacement caused by a shear wave.

The processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, combinations thereof or other now known or later developed device for detecting and processing information for display from beamformed ultrasound samples.

In one embodiment, the processor 18 includes one or more detectors and a separate processor. The separate processor is a control processor, general processor, digital signal processor, application specific integrated circuit, field programmable gate array, network, server, group of processors, data path, combinations thereof or other now known or later developed device for determining displacement, and calculating tissue properties. For example, the separate processor performs any combination of one or more of the acts shown in FIG. 1. The processor 18 is configured by software and/or hardware to perform the acts.

In one embodiment, the processor 18 estimates tissue displacements as a function of the output data from the receive beamformer 16. The displacements are estimated as a profile or data representing a curve of magnitude of displacement as a function of time. The displacement profile may be obtained by correlating or otherwise determining level of similarity between reference data and data obtained during passing of the shear wave. The processor 18 uses the displacement information from multiple locations. Correlation coefficients for at least one pair of the tissue displacements from different ones of the spatial locations are determined. The correlation coefficients from different pairs are used to solve for a traveling time. The traveling time for different spatial locations is solved at a same time, such as being output from an equation with the same inputs. The traveling time for different spatial locations are provided in an output set determined from a function using data from the different ones of the spatial locations. Each value of the output set is a function of the tissue displacements for a plurality of spatial locations, including spatial locations not defining the distance for which travel time is calculated. Displacement for different ones of the spatial locations contributes to a given traveling time. For example, the correlation coefficients are computed for at least three pairs of tissue displacements: a first pair being displacements in tissue at a same location caused by transmissions at different locations, a second pair being displacements in tissue at different locations caused by transmissions at a same location, and a third pair being displacements in tissue at different locations caused by transmissions at other different locations.

The processor 18 calculates shear velocity from the traveling time. Other shear information may be determined. The delays associated with particular scan lines are determined. The shear velocity is calculated from the delays and corresponding distances or ranges.

The processor 18 generates and outputs image or display values mapped from the tissue properties to the display 20. For example, the shear velocity, shear modulus, or other value is determined for each location. The magnitude of the values modulates the color, hue, brightness, and/or other display characteristic. The processor 18 determines a pixel value (e.g., RGB) or a scalar value converted to a pixel value. The image is generated as the scalar or pixel values. The image may be output to a video processor, look-up table, color map, or directly to the display 20.

The processor 18 operates pursuant to instructions stored in the memory 22 or another memory. The processor 18 is programmed for solving for shear wave information in medical ultrasound imaging. The memory 2 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 20 is a CRT, LCD, projector, plasma, or other display for displaying two-dimensional images or three-dimensional representations. The display 20 displays one or more images representing shear information, such as the shear velocity.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A system for solving for shear wave information in medical ultrasound imaging, the system comprising:
   a receive beamformer operable to output data representing spatial locations as a function of received acoustic signals;
   a processor configured to estimate tissue displacements due to a shear wave as a function of a level of similarity between sets of the output data, compute correlation coefficients of at least one pair of the processor estimated tissue displacements from different ones of the spatial locations, solve for a traveling time of the shear wave based on the correlation coefficients, and generate an image as a function of the traveling time; and
   a display operable to display the image.

2. The system of claim 1 wherein the processor is configured to solve for the different ones of the spatial locations at a same time.

3. The system of claim 2 wherein the processor is configured to solve for the different ones of the spatial locations with an output set determined from a function using data from the different ones of the spatial locations, where each value of the output set is a function of the tissue displacements for the different ones of the spatial locations.

4. The system of claim 1 wherein the processor is configured to compute the correlation coefficients for at least three pairs of the tissue displacements, a first pair being displacements in tissue at a same location caused by transmissions at different locations, a second pair being displacements in tissue at different locations caused by transmissions at a same location, and a third pair being displacements in tissue at different locations caused by transmissions at other different locations.

5. The system of claim 1 wherein the processor is configured to calculate shear velocity from the traveling time, the image generated to represent the shear velocity.

6. The system of claim 1 wherein the processor is configured to estimate the tissue displacements by tracking a magnitude of tissue movement over time.

7. The system of claim 1 wherein the processor is configured to estimate the tissue displacements caused by ultrasound transmissions.

8. The system of claim 1 wherein the processor is configured to compute the correlation coefficients for at least one pair of shear wave displacement temporal profiles.

* * * * *